United States Patent [19]  [11] 4,013,619
Schmidt  [45] Mar. 22, 1977

[54] PHENOL ACETALS
[75] Inventor: Andreas Schmidt, Reinach, Switzerland
[73] Assignee: Ciba-Geigy Corporation, Ardsley, N.Y.
[22] Filed: Jan. 20, 1975
[21] Appl. No.: 542,631
[30] Foreign Application Priority Data
　　　Jan. 21, 1974　Switzerland ............ 788/74
[52] U.S. Cl. .............. 260/45.8 A; 260/248 A; 260/327 M; 260/340.7
[51] Int. Cl.² ......................... C08K 5/13
[58] Field of Search .......... 260/340.7, 45.8 A

[56] References Cited
UNITED STATES PATENTS

| 3,347,871 | 10/1967 | Harding | 260/340.7 |
| 3,388,098 | 6/1968 | Harding | 260/340.7 X |
| 3,401,147 | 9/1968 | Smith et al. | 260/340.7 X |
| 3,767,615 | 10/1973 | Throckmorton et al. | 260/45.8 AX |

FOREIGN PATENTS OR APPLICATIONS

| 2,157,939 | 8/1973 | France | 260/340.7 |

Primary Examiner—Ethel G. Love
Attorney, Agent, or Firm—Luther A. R. Hall

[57] ABSTRACT

Compounds of the general formula I (I)

in which $R_1$ and $R_5$ independently of one another denote hydrogen or lower alkyl, one of $R_2$ and $R_3$ denotes hydroxyl and the other denotes alkyl, cycloalkyl or aralkyl, $R_4$ denotes hydrogen or, if $R_3$ denotes hydroxyl, additionally also denotes alkyl, cycloalkyl or aralkyl, X denotes the direct bond, or a group $$R_8-\underset{|}{\overset{|}{C}}-R_9$$

wherein $R_8$ is hydrogen, alkyl, aralkyl or phenyl and $R_9$ is hydrogen, alkyl, aralkyl, phenyl or the group wherein $R_1$–$R_5$ have the above meaning, of $R_9$ conjointly with $R_8$ is alkylene, Y denotes oxygen or sulfur, $n$ denotes 1, 2, 3 or 4, $R_6$ denotes the acid radical of an n-valent organic oxygen acid or, if $n$ is equal to 1, additionally also denotes hydroxyl or, if $n$ is equal to 2, additionally also denotes —O—, and $R_7$ denotes a lower alkyl group having 1–3 carbon atoms, or, if $n$ is equal to 1, additionally also denotes, conjointly with $R_6$, a group Ia (Ia)

wherein $R_1$–$R_5$, X and Y have the above meaning, or if $n$ is equal to 1 and Y denotes oxygen, additionally also denotes, conjointly with $R_6$, a group Ib (Ib)

wherein $R_1$–$R_5$ and X have the above meaning, and $R_{10}$ is hydroxyl or the acid radical of a monovalent organic oxygen acid, for stabilising organic material.

6 Claims, No Drawings

PHENOL ACETALS

The invention relates to new phenol acetals, a process for their manufacture, their use for the protection of substrates which are sensitive to oxidation and, as an industrial product, the substrates which are protected with their aid.

It is known, for example, from German Patent Specification 1,201,349, to employ derivatives of sterically hindered phenols as stabilisers for organic materials, such as polymers, against thermo-oxidative degradation thereof or against ageing thereof by light. It is also known, for example, from DOS 2,059,916, to use acetals and thioacetals of alkylated p-hydroxybenzaldehydes. However, the stabilising effect of this last-named class of compounds is completely inadequate. On the other hand, many phenol derivatives exhibit the disadvantage that they objectionably discolour the organic material to be protected, either already when being incorporated or when exposed to light or when they are in contact with industrial waste gases or also when they are in contact with hot water, which greatly limits their industrial applicability. Surprisingly, new compounds have been found which far exceed in effectiveness the known derivatives of p-hydroxybenzaldehyde and which are also distinguished by a significantly better colour stability at elevated temperatures.

The new compounds correspond to the general formula I

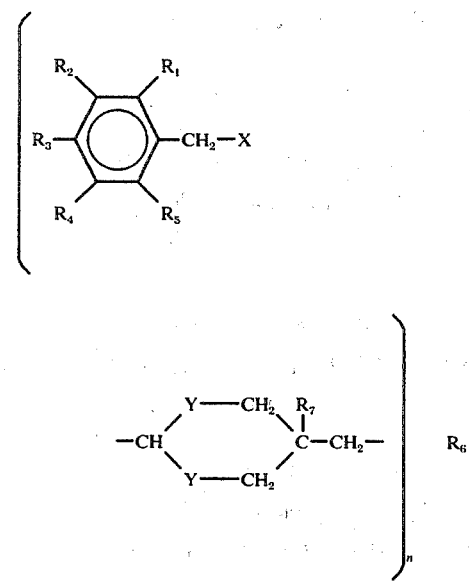

in which $R_1$ and $R_5$ independently of one another denote hydrogen or lower alkyl, one of $R_2$ and $R_3$ denotes hydroxyl and the other denotes alkyl, cycloalkyl or aralkyl, $R_4$ denotes hydrogen or, if $R_3$ denotes hydroxyl, additionally also denotes alkyl, cycloalkyl or aralkyl, X denotes the direct bond, or a group

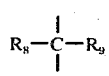

wherein $R_8$ is hydrogen, alkyl, aralkyl or phenyl and $R_9$ is hydrogen, alkyl, aralkyl, phenyl or the group

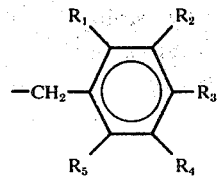

wherein $R_1 - R_5$ have the above meaning, or $R_9$ conjointly with $R_8$ is alkylene, Y denotes oxygen or sulphur, $n$ denotes 1, 2, 3 or 4, $R_6$ denotes the acid radical of an n-valent organic oxygen acid or, if $n$ is equal to 1, additionally also denotes hydroxyl or, if $n$ is equal to 2, additionally also denotes —O—, and $R_7$ denotes a lower alkyl group having 1 – 3 carbon atoms, or, if $n$ is equal to 1, additionally also denotes, conjointly with $R_6$, a group Ia

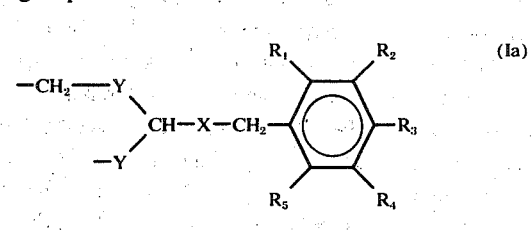

wherein $R_1 - R_5$, X and Y have the above meaning, or, if $n$ is equal to 1 and Y denotes oxygen, additionally also denote, conjointly with $R_6$, a group Ib

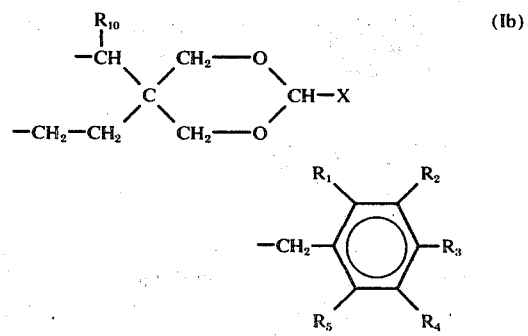

wherein $R_1 - R_5$ and X have the above meaning, and $R_{10}$ is hydroxyl or the acid radical of a monovalent organic oxygen acid.

Compounds of the formula I which are preferred are those in which $R_1$ and $R_5$ independently of one another denote hydrogen or methyl, one of $R_2$ and $R_3$ denotes hydroxyl and the other denotes alkyl having 1 – 8 carbon atoms, cycloalkyl having 6 – 8 carbon atoms or aralkyl having 7 – 9 carbon atoms, $R_4$ denotes hydrogen or, if $R_3$ denotes hydroxyl, additionally also denotes alkyl having 1 – 8 carbon atoms, cycloalkyl having 6 – 8 carbon atoms or aralkyl having 7 – 9 carbon atoms, X denotes the direct bond or a group

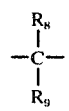

wherein $R_8$ is hydrogen, alkyl having 1 – 8 carbon atoms, aralkyl having 7 – 9 carbon atoms, or phenyl, and $R_9$ is hydrogen, alkyl having 1 – 8 carbon atoms, aralkyl having 7 – 9 carbon atoms, phenyl or the group

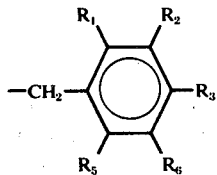

or, conjointly with $R_8$, is alkylene having 2 – 11 carbon atoms, Y denotes oxygen or sulphur, $n$ denotes 1, 2, 3 or 4, $R_6$ denotes, if $n$ is equal to 1, hydroxyl or a group $R_{11}$—COO— in which $R_{11}$ denotes alkyl having 1 – 21 carbon atoms, alkenyl having 2 – 17 carbon atoms, cycloalkyl having 5 – 6 carbon atoms, benzyl thiaalkyl having 2 – 20 carbon atoms, oxaalkyl having 2 – 20 carbon atoms, phenyl, hydroxyphenyl, chlorophenyl, dichlorophenyl, alkylphenyl having 7 – 14 carbon atoms, alkoxyphenyl having 7 – 24 carbon atoms, acyloxyphenyl having 8 – 24 carbon atoms, carbalkoxyphenyl having 8 – 25 carbon atoms, α-naphthyl, β-naphthyl, alkylamino having 1 – 18 carbon atoms, cyclohexylamino, benzylamino, anilino, chloroanilino, dichloroanilino, alkylanilino having 7 – 10 carbon atoms, or naphthylamino or $R_6$ denotes, if $n$ is equal to 2, —O— or a group

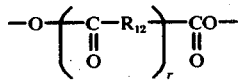

in which $r$ denotes zero or 1, and $R_{12}$ denotes a direct bond, alkylene having 1 – 8 carbon atoms, phenylene, naphthylene; alkylenediamino having 2 – 9 carbon atoms, phenylenediamino, toluylenediamino, naphthylenediamino, diphenylmethane-4,4'-diamino or the radical

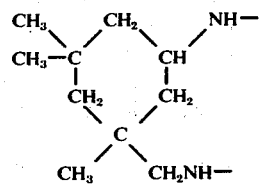

or $R_6$ denotes, if $n$ is equal to 3, one of the groups

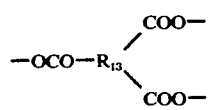

or

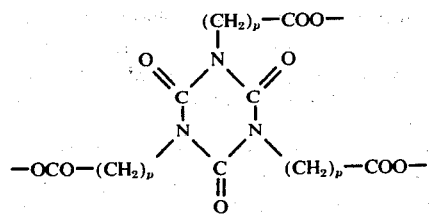

in which $p$ denotes 1 or 2, and $R_{13}$ denotes alkanetriyl having 2 – 6 carbon atoms, cycloalkanetriyl having 3 – 6 carbon atoms or phenyltriyl, or $R_6$ denotes, if $n$ is equal to 4, a group

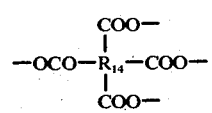

in which $R_{14}$ denotes alkanetetrayl having 2 – 6 carbon atoms, or phenyltetrayl, and $R_7$ denotes a lower alkyl group having 1 – 3 carbon atoms, or, if $n$ is equal to 1, additionally also denotes, conjointly with $R_6$, a group Ia

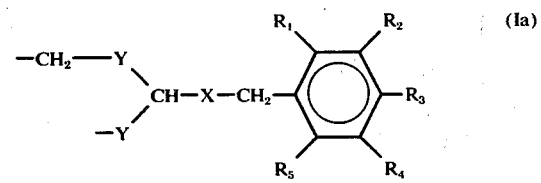

or, if $n$ is equal to 1 and Y denotes oxygen, additionally also denotes conjointly with $R_6$, a group Ib

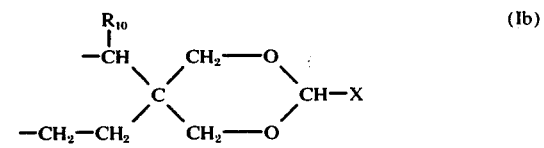

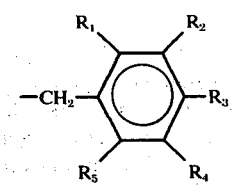

wherein $R_{10}$ is hydroxyl or a group $R_{11}$—COO— having the above meaning for $R_{11}$.

Particularly preferred compounds are those of the formula

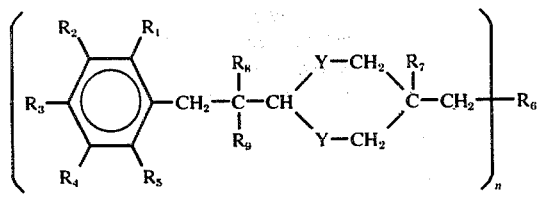

in which $R_1$ and $R_5$ independently of one another denote hydrogen or methyl, one of $R_2$ and $R_3$ denotes hydroxyl and the other denotes alkyl having 1 – 4 carbon atoms, $R_4$ denotes hydrogen or, if $R_3$ denotes hydroxyl, additionally also denotes alkyl having 1 – 4 carbon atoms, $R_8$ denotes alkyl having 1 – 4 carbon atoms, or phenyl, $R_9$ denotes alkyl having 1 – 4 carbon atoms, phenyl or the group

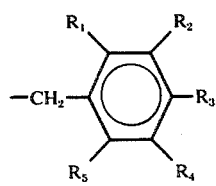

or denotes, conjointly with $R_8$, alkylene having 4 or 5 carbon atoms, Y denotes oxygen or sulphur, $n$ denotes 1 or 2, $R_6$ denotes, if $n$ is equal to 1, hydroxyl or a group $R_{11}$— Coo — in which $R_{11}$ denotes alkyl having 1 – 17 carbon atoms, cyclohexyl, benzyl, phenyl, alkylphenyl having 7 – 14 carbon atoms, alkoxyphenyl having 7 – 24 carbon atoms, acyloxyphenyl having 8 – 24 carbon atoms, carbalkoxyphenyl having 8 – 25 carbon atoms, α-naphthyl, β-naphthyl, alkylamino having 1 – 18 carbon atoms, cyclohexylamino, anilino, chloroanilino or naphthylamino, or $R_6$ denotes, if $n$ is equal to 2, —O— or a group $$-O-\left[-\overset{\underset{\parallel}{O}}{C}-R_{12}-\right]_r\overset{\underset{\parallel}{O}}{C}O-$$

in which $r$ denotes zero or 1, and $R_{12}$ denotes the direct bond, alkylene having 1 – 8 carbon atoms, phenylene, naphthylene, alkylenediamino having 2 – 9 carbon atoms, toluylenediamino or diphenylmethane-4,4'-diamino, and $R_7$ denotes a lower alkyl group having 1 – 3 carbon atoms, or, if $n$ is equal to 1, additionally also denotes, conjointly with $R_6$, a group Ia

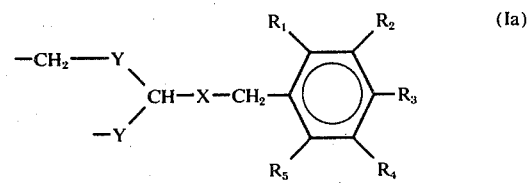

or, if $n$ is equal to 1 and Y denotes oxygen, additionally also denotes, conjointly with $R_6$, a group Ib

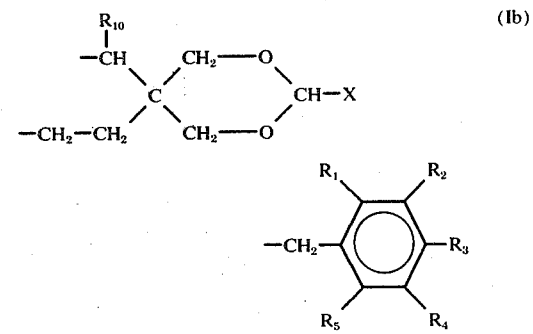

wherein $R_{10}$ is hydroxyl or a group $R_{11}$—COO— having the above meaning for $R_{11}$.

Among the compounds which are particularly preferred, compounds of the following formula should be mentioned above all:

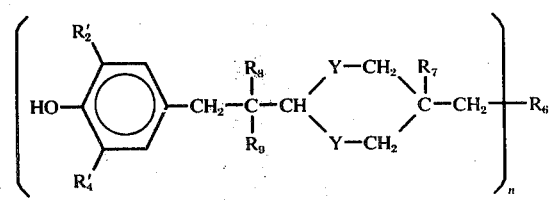

in which $R_2'$ denotes alkyl having 1 – 4 carbon atoms, $R_4'$ denotes alkyl having 3 – 4 carbon atoms, $R_8$ denotes alkyl having 1 – 4 carbon atoms, $R_9$ denotes alkyl having 1 – 4 carbon atoms, or, conjointly with $R_8$, denotes pentamethylene, Y denotes oxygen or sulphur, $n$ denotes 1 or 2, $R_6$ denotes, if $n$ is equal to 1, hydroxyl or a group $R_{11}$—COO—, in which $R_{11}$ denotes alkyl having 1 – 7 carbon atoms, benzyl, phenyl, alkylamino having 1 – 18 carbon atoms, or anilino, or $R_6$ denotes, if $n$ is equal to 2, —O— or a group

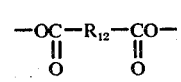

in which $R_{12}$ denotes the direct bond, alkylene having 1 – 8 carbon atoms, phenylene or alkylenediamino having 2 – 6 carbon atoms, and $R_7$ denotes a lower alkyl group having 1 – 3 carbon atoms, or, if $n$ is equal to 1, additionally also denotes, conjointly with $R_6$, a group

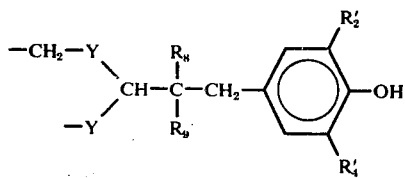

or, if $n$ is equal to 1 and Y denotes oxygen, additionally also denotes, conjointly with $R_6$, a group

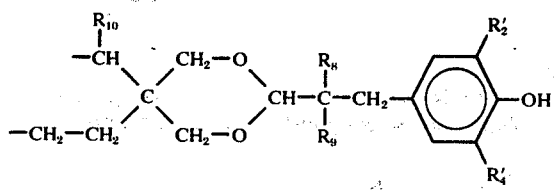

wherein $R_{10}$ is hydroxyl or group $R_{11}$—COO— having the above meaning for $R_{11}$, and compounds should be mentioned very particularly in which $R_2'$ denotes methyl, isopropyl or tert.butyl $R_4'$ denotes tert.butyl, $R_8$ denotes methyl, $R_9$ denotes methyl, Y denotes O or S, $n$ denotes 1 or 2, $R_6$ denotes, if $n$ is equal to 1, hydroxyl or a group $R_{11}$—COO— in which $R_{11}$ denotes alkyl having 1 – 7 carbon atoms, or phenyl, or $R_6$ denotes, if $n$ is equal to 2, —O— or a group —OCO—$R_{12}$—COO— in which $R_{12}$ denotes the direct bond, alkylene having 1 – 8 carbon atoms, or phenylene, and $R_7$ denotes methyl, ethyl, propyl or, if $n$ is equal to 1, additionally also denotes, conjointly with $R_6$, a group

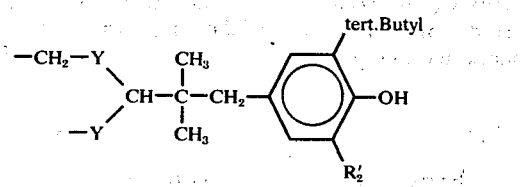

or, if $n$ is equal to 1 and Y is equal to 0, additionally denotes, conjointly with $R_6$, a group

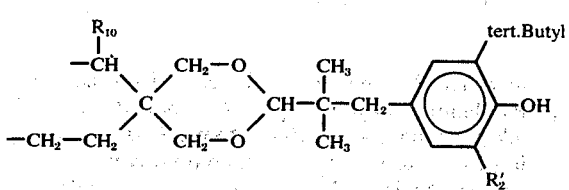

wherein $R_2'$ has the above meaning and $R_{10}$ is hydroxyl or a group $R_{11}$—COO— having the above meaning for $R_{11}$.

The following are examples of compounds of the formula I: 3,9-bis-(3-methyl-4-hydroxy-5-tert.butylbenzyl)-2,4,8,10-tetra-oxaspiro[5,5]undecane 3,11-bis-(2,3-dimethyl-4-hydroxy-5-tert.butylbenzyl)-7-hydroxy-2,4,10,12-tetraoxadispiro[5,1,5,3]hexadecane, 3,9-bis-(2,6-dimethyl-3-hydroxy-4-tert.butylbenzyl)-2,4,8,10-tetraoxaspiro[5,5]undecane, 2-[1,1-dimethyl-2-(3,5-ditert.butyl-4-hydroxyphenyl)-ethyl]-5-stearroyloxymethyl-5-methyl-1,3-dioxacyclohexane, 2-[2-(3-methyl-4-hydroxy-5-tert.butylphenyl)ethyl]-5-hydroxymethyl-5-methyl-1,3-dioxacyclohexane, 3,9-bis-[1,1-dimethyl-2-(3-tert.-butyl- 4-hydroxy-5-methylphenyl)-ethyl]-2,4,8,10-tetra-oxa-spiro[5,5]-undecane, 3,9-bis-[1,1-dimethyl-2-(3,5-di-isopropyl-4-hydroxyphenyl)-ethyl]-2,4,8,10-tetra-oxaspiro[3,5]undecane, 2-[1,1-dimethyl-2-(3,5-ditert.butyl-4-hydroxyphenyl)-ethyl]-5-benzoyloxymethyl-5-methyl-1,3-dioxacylohexane, adipic acid bis-[2[1,1-dimethyl-2-(3-methyl-4-hydroxy-5-tert.butyl-phenyl)ethyl]-5-ethyl-1,3-dioxacyclohex-5-yl-methyl ester], N,N'-hexamethylene-bis-[carbamic acid 2[1,1-dimethyl-2-(3,5-ditert.butyl-4-hydroxyphenyl)ethyl]-5-ethyl-1,3-dioxacyclohex-5-yl-methyl ester], 3,9-bis-[1,1-dimethyl-2-(3,5-ditert. butyl-4-hydroxyphenyl)-ethyl]-2,4,8,10-tetra-thia-spiro-[5,5]-undecane, 3,9-bis-[1-(3,5-ditert.butyl-4-hydroxybenzyl)-cyclohexyl]-2,4,8,10-tetraoxaspiro[5,5]undecane and 3,9-bis-[1,1-dimethyl-2-(3,5-ditert.-butyl-4-hydroxyphenyl)-ethyl]-2,4,8,10-tetra-oxa-spiro[5,5]undecane.

In the definition of the compounds of the formula I, $R_1$ and $R_5$ can be lower alkyl. This can be lower alkyl having 1 to 6 carbon atoms, such as methyl, ethyl, n-propyl, n-butyl, n-amyl or hexyl. $R_7$ as lower alkyl can be methyl, ethyl or n-propyl, for example.

If $R_2$, $R_3$, $R_4$, $R_8$, $R_9$ and/or $R_{11}$ denote alkyl, it is, for example methyl, ethyl, iso-propyl, n-butyl, sec.-butyl, tert.-butyl, n-amyl, tert.-amyl, sec.-amyl, hexyl, octyl, tert.-octyl, decyl, dodecyl, tetradecyl or octadecyl.

$R_2$, $R_3$, $R_4$ and/or $R_{11}$ can denote cycloalkyl groups, such as cyclopentyl, cyclohexyl, α-methylcyclohexyl or cyclooctyl.

$R_2$, $R_3$, $R_4$, $R_8$ and/or $R_9$ can be aralkyl groups, such as; for example, benzyl, α-phenylethyl or α,α-dimethylbenzyl.

$R_{12}$ and/or $R_8$, conjointly with $R_9$, also have the meaning of alkylene, such as ethylene, trimethylene, tetramethylene, pentamethylene, 1-methyltetramethylene or 2,2-dimethyltrimethylene.

$R_{11}$ in the meaning of thiaalkyl can be, for example, 3-thiabutyl, 3-thiapentyl, 3-thiaheptyl, 3-thiaundecyl, 3-thiapentadecyl, 3-thianonadecyl or 3-thiaheneicosyl, and, in the meaning of oxaalkyl, can be 3-oxabutyl, 2-oxapentyl, 2-oxaheptyl, 3-oxapentadecyl or 2-oxaheneicosyl.

$R_{11}$, in the meaning of alkenyl, can be vinyl, propenyl or butenyl.

If $R_{11}$ is hydroxyphenyl, chlorophenyl or dichlorophenyl, it can be o-, m- or p-hydroxyphenyl, o-, m- or p-chlorophenyl or 2,4-dichlorophenyl.

$R_{11}$, in the meaning of alkylphenyl, is, for example, o-, m- or p-alkylphenyl, it being possible for alkyl to be methyl, ethyl, iso-propyl, butyl, sec.-butyl, tert.-butyl, amyl, tert.-amyl, sec.-amyl, hexyl, octyl or tert.-octyl.

If $R_{11}$ denotes alkoxyphenyl, the alkoxy group can be in the o-, m- or p-position in the phenyl radical, the alkoxy group being, for example, methoxy, ethoxy, propoxy or butoxy.

If $R_{11}$ is acyloxyphenyl, the acyloxy radical is in the o-, m- or p-position in the phenyl radical. Acyl is, for example, the radical of an aliphatic or aromatic carboxylic acid having 2 to 18 carbon atoms, for example of an alkanoic acid, such as acetic acid, propionic acid, caproic acid, lauric acid or stearic acid or of an unsubstituted or substituted benzoic acid, such as benzoic acid, p-tert.butylbenzoic acid or p-tert.octylbenzoic acid.

If $R_{11}$ denotes carbalkoxyphenyl, the carbalkoxy radical is in the o-, m- and p-position in the phenyl radical. It can be carbomethoxy, carboethoxy, carbopropoxy or carbobutoxy.

As alkylamino, $R_{11}$ has, in particular, 1 to 18 carbon atoms, for example methylamino, ethylamino, butylamino, amylamino, hexylamino, octylamino, decylamino, dodecylamino, tetradecylamino or octadecylamino.

$R_{11}$, in the meaning of alkylanilino, is o-, m- or p-alkylanilino, it being possible for alkyl to be, in particular, lower alkyl, such as methyl, ethyl, propyl or butyl.

As alkylenediamino, $R_{12}$ has, in particular, 1 to 4 carbon atoms and is, for example, ethylenediamino, 1,3-propylenediamino or 1,4-tetramethylenediamino.

If $R_{13}$ denotes alkanetriyl, it is, for example, ethanetriyl, propanetriyl or butanetriyl, and, if it denotes cycloalkanetriyl, it is, for example, cyclohexanetriyl.

As alkanetetrayl, $R_{14}$ can be, for example, ethanetetrayl, propanetetrayl or butanetetrayl.

The compounds of the formula I in which $n$ denotes 1 or 2, $R_6$ denotes, if $n$ is equal to 1, -OH or denotes, if $n$ is equal to 2, —O—, and $R_7$ denotes a lower alkyl group having 1 to 3 carbon atoms, or, if $n$ is equal to 1, additionally denotes, conjointly with $R_6$, a group I$a$, or, if $n$ is equal to 1 and Y denotes oxygen, additionally denotes, conjointly with $R_6$, a group I$b$ in which $R_{10}$ is hydroxyl, are prepared by reacting, in a solvent and in the presence of an acid catalyst, a compond of the formula II

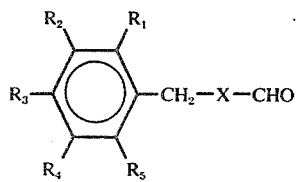

with a compound of the formula III

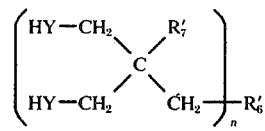

wherein $n$ denotes 1 or 2, Y denotes oxygen or sulphur, $R_6'$ denotes, if $n$ is equal to 1 and Y is oxygen, the group —OH, or, if $n$ is equal to 1, Y is sulphur and $R_7'$ is the group —CH$_2$—SH, also denotes the group —SH, or, if $n$ is equal to 2, denotes the group —O—, $R_7'$ denotes lower alkyl having 1 – 3 carbon atoms, or the group

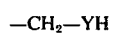

or, of $n$ is equal to 1 and Y is oxygen, denotes, conjointly with $R_6'$, the group

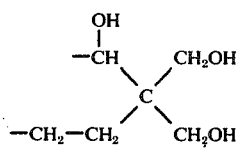

the compounds of the formulae II and III being employed in a molar ratio of 1:1 or 2:1.

Compounds of the formula I in which $n$ denotes 1, 2, 3 or 4, $R_6$ denotes the acid radical of an n-valent organic oxygen acid, and $R_7$ denotes a lower alkyl group having 1 – 3 carbon atoms, or, if $n$ is equal to 1 and Y denotes oxygen, additionally also denotes, conjointly with $R_6$, the group I$b$

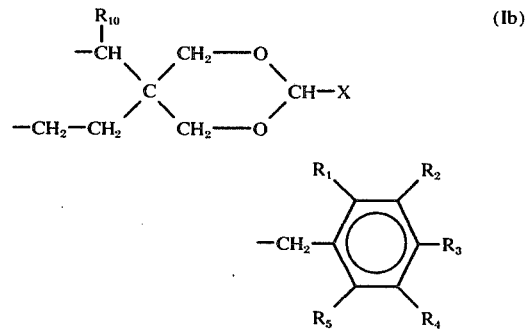

wherein $R_{10}$ is the acid radical of a 1-valent organic oxygen acid, are prepared by esterifying the compounds which contain hydroxyl groups and which, as described above, are obtained in $R_6$ or/and $R_{10}$, with an n-valent organic oxygen acid or a reactive derivative thereof, such as an ester or halide.

The reactions are carried out according to the generally known processes for esterification or transesterification reactions.

The following are suitable solvents which can be used in the reaction of compounds of the formulae II and III: aromatic hydrocarbons, such as benzene, toluene or xylene, aliphatic hydrocarbons, such as hexane, cyclohexane, heptane, octane or ligroin, ketones, such as acetone, methyl ethyl ketone, or cyclohexanone, alcohols, such as methanol, ethanol, isopropanol, butanol or cyclohexanol, ethers, such as diethyl ether, dioxane or tetrahydrofurane, esters, such as ethyl acetate or amyl acetate, and the like.

It is preferable to use solvents which are suitable for the azeotropic distillation of the water liberated during the reaction, such as, for example, benzene, toluene, xylene, n-propanol, isopropanol, methyl ethyl ketone, ethyl acetate, n-butanol, dioxane, n-hexane or cyclohexane.

The water formed in the reaction of compounds of the formulae II and III can also be removed with the aid of an inert drying agent which is added during the reaction, such as, for example, calcium chloride, sodium sulphate and the like.

The acid catalyst is employed in a concentration of 0.1 – 10 mol %, preferably 0.5 – 5 mol %, particularly preferentially 1 – 3 mol %, calculated on the aldehyde of the formula II. The following are examples of acid catalysts which can be used: anhydrous hydrochloric acid, sulphuric acid, orthophosphoric acid, pyrophosphoric acid, chloroacetic acid, benzenesulphonic acid, p-bromobenzenesulphonic acid and p-toluenesulphonic acid.

If the water split off is removed by azeotropic distillation, the temperature at which the reaction is carried out is given by the boiling point of the solvent used or of its azeotrope with water. The reaction is preferably carried out in solvents having boiling points between 70° and 140° C. If the water split off is removed by means of a drying agent, temperatures from 0° C to 150° C, preferably 20° C to 70° C, are used.

The starting materials of the formulae II and III are known or can be prepared by known processes.

Organic materials, such as, for example, the following polymers, can be stabilised using the compounds of the formula I.

1. Polymers which are derived from hydrocarbons with single or double unsaturation, such as polyolefines, for example, polyethylene, which can optionally be crosslinked, polypropylene, polyisobutylene, polymethylbutene-1, polymethylpentene-1, polybutene-1, polyisoprene, polybutadiene, polystyrene, polyisobutylene, copolymers of the monomers on which the homopolymers mentioned are based, such as ethylene-propylene copolymers, propylene-butene-1copolymers, propylene-isobutylene copolymers, styrene-butadiene copolymers and terpolymers of ethylene and propylene with a diene, such as, for example, hexadiene, dicyclopentadiene or ethylidenenorbornene; mixtures of the abovementioned homopolymers, such as, for example, mixtures of polypropylene and polyethylene, polypropylene and polybutene-1, or polypropylene and polyisobutylene.

2. Vinyl polymers containing halogen, such as polyvinyl chloride, polyvinylidene chloride, polyvinyl fluoride, but also polychloroprene and chlorinated rubbers.

3. Polymers which are derived from $\alpha,\beta$-unsaturated acids and their derivatives, such as polyacrylates and polymethacrylates, polyacrylamides and polyacrylonitrile, as well as their copolymers with other vinyl compounds, such as acrylonitrile/butadiene/styrene, acrylonitrile/styrene and acrylonitrile/styrene/acrylic ester copolymers.

4. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers.

6. Polyacetals, such as polyoxymethylene and polyoxyethylene, as well as those polyoxymethylenes which contain ethylene oxide as the comonomer.

7. Polyphenylene oxides.

8. Polyurethanes and polyureas.

9. Polycarbonates.

10. Polysulphones.

11. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

12. Polyesters which are derived from dicarboxylic acids and dialcohols and/or from hydroxycarboxylic acids or the corresponding lactones, such as polyethylene glycol terephthalate or poly-1,4-dimethylolcyclohexane terephthalate.

13. Crosslinked polymers which are derived from aldehydes on the one hand and phenols, ureas and melamines on the other, such as phenol-formaldehyde, urea-formaldehyde and melamine-formaldehyde resins.

14. Alkyd resins, such as glycerine-phthalic acid resins and their mixtures with melamine-formaldehyde resins.

15. Unsaturated polyester resins which are derived from copolyesters of saturated and unsaturated dicarboxylic acids with polyhydric alcohols, with vinyl compounds as crosslinking agents, and also their halogen-containing modifications of low inflammability.

16. Natural polymers such as cellulose, rubber, proteins and their polymer-homologously chemically modified derivatives, such as cellulose acetates, cellulose propionates and cellulose butyrates, or the cellulose ethers, such as methylcellulose.

17. High molecular monomeric substances, for example mineral oils, animal and vegetable fats, oils and waxes, or oils, waxes and fats based on synthetic esters.

The compounds of the formula I are incorporated in the substrates in a concentration of 0.005 to 5% by weight, relative to the material to be stabilised.

Preferably, 0.01 to 1.0, particularly preferably 0.02 to 0.5, % by weight of the compounds, relative to the material to be stabilised, are incorporated into the latter. The incorporation can be carried out, for example, by mixing in at least one of the compounds of the formula I and optionally further additives by the methods customary in the art, before or during shaping, or by applying the compounds, dissolved or dispersed, to the polymer, where appropriate with subsequent evaporation of the solvent.

In the case of crosslinked polyethylene, the compounds are added before the crosslinking.

The compounds of the formula I can also be added before or during the polymerisation, it being possible, by a potential incorporation into the polymer chain, to obtain stabilised substrates in which the stabilisers are not volatile or capable of extraction.

The following may be mentioned as examples of further additives with which the compounds of the formula I can be co-employed:

1. antioxidants 1.1. Simple 2,6-dialkyphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl4-methylphenol.

1.2. Derivatives of alkylated hydroquinones, such as, for example, 2,5-di-tert.-butyl-hydroquinone, 2,5-di-tert.-amylhyroquinone, 2,6-di-tert.-butyl-hydroquinone, 2,5-di-tert.butyl-4-hydroxy-anisole, 3,5-di-tert.-butyl-4-hydroxy-anisole, tris(3,5-di-tert.-butyl-4-hydroxyphenyl)-phosphite, 3,5-di-tert.-butyl-4-hydroxyphenyl stearate and bis-(3,5-di-tert.-butyl-4-hydroxyphenyl) adipate.

1.3. Hydroxylated thiodiphenyl ethers, such as, for example, 2,2'-thio-bis-(6-tert.-butyl-4-methylphenol), 2,2'-thio-bis(4-octylphenol), 4,4'-thio-bis(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl)-disulphide.

1.4. Alkylidene-bisphenols, such as, for example, 2,2'-methylene-bis-(6-tert.butyl-4-methylphenol)-2,2'-methylene-bis-(6-tert.butyl-4-ethylphenol), 4,4'-methylene-bis-(6-tert.butyl-2-methylphenol), 4,4'-methylene-bis-(2,6-di-tert.butyl-phenol), 2,6-di-(3-tert.butyl-5-methyl-2-hydroxybenzyl)- 4-methylphenol, 2,2'-methylene-bis-[4-methyl-6-(α-methyl-cyclohexyl)-phenol], 1,1-bis-(3,5-dimethyl-2-hydroxyphenyl)butane, 1,1-bis-(5-tert.butyl-4-hydroxy-2-methylphenyl)-butane, 2,2-bis-(5-tert.butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert. butyl-4-hydroxy-2-methylphenyl)-4-n-dodecylmercapto-butane, 1,1,5,5-tetra-(5-tert.butyl-4-hydroxy-2-methylphenyl)-pentane and ethylene glycol bis-[3,3-bis-(3'-tert.butyl-4'-hydroxyphenyl)-butyrate].

1.5. O-, N- and S-benzyl compounds, such as, for example, 3,5,3',5',-tetra-tert.butyl-4,4'-dihydroxydibenzyl ether, 4-hydroxy-3,5-dimethylbenzyl-mercaptoacetic acid octadecyl ester, tris-(3,5-di-tert.butyl-4-hydroxybenzyl)-amine and bis-(4-tert.butyl-3-hydroxy-2,6-dimethylbenzyl)-dithioterephthalate.

1.6. Hydroxybenzylated malonic esters, such as, for example, 2,2-bis-(3,5-di-tert.butyl-2-hydroxybenzyl)-malonic acid dioctadecyl ester, 2-(3-tert.butyl-4-hydroxy-5-methylbenzyl)-malonic acid dioctadecyl ester, 2,2-bis-(3,5-di-tert.butyl-4-hydroxybenzyl)-malonic acid didocylmercaptoethylester and 2,2-(3,5-di-tert.butyl-4-hydroxybenzyl)malonic acid di-[4-(1,1,3,3-tetramethylbutyl)-phenyl]-ester.

1.7. such as, for example, 1,3,5-tri-(3,5-di-tert.butyl-4-hydroxybenzyl)-2,4,6-trimethylbenzene, 1,4-di-(3,5-di-tert.butyl-4-hydroxybenzyl)-2,3,5,6-tetramethylbenzene and 2,4,6-tri-(3,5-di-tert.butyl-4-hydroxybenzyl)-phenol.

1.8. s-Triazine compounds, such as, for example, 2,4-bis-octylmercapto-6-(3,5-di-tert.butyl-4-hydroxy-anilino)-s-triazine, 2-ocytlmercapto-4,6-bis-(3,5-di-tert.butyl-4-hydroxy-anilino)-s-triazine, 2-octylmercapto-4,6-bis-(3,5-di-tert.butyl-4-hydroxy-phenoxy)-s-triazine, 2,4,6-tris-(3,5-di-tert.butyl-4-hydroxyphenoxy)-s-triazine, 2,4,6-tris-(3,5-di-tert.butyl-4-hydroxyphenylethyl)-s-triazine and 1,3,5-tris-(3,5-di-tert.butyl-4-hydroxybenzyl)-ioscyanurate.

1.9. Amides of β-(3,5-di-tert.butyl-4-hydroxyphenyl)-propionic acid, such as, for example, 1,3,5-tris-(3,5-di-tert.butyl-4-hydroxyphenyl-propionyl)-hexahydro-s-triazine and N,N'-di-(3,5-di-tert.butyl-4-hydroxyphenyl-propionyl)-hexamethylenediamine.

1.10. Esters of β-(3,5-di-tert.butyl-4-hydroxyphenyl)-propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecaonol, 3-thia-pentadecanol, tirmethylhexanediol, trimethylolethane, trimethylolpropane, trishydroxyethyl isocyanurate and 4-hydroxymethyl-1-phospha-2,6,7-trioxabicyclo[2,2,2]octane.

1.11. Esters of β-(5-tert.butyl-4-hydroxy-3-methylphenyl propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, trishydroxyethyl isocyanurate and 4-hydroxymethyl-1-phospha-2,6,7-trioxabicyclo[2,2,2]octane.

1.12. Esters of 3,5-di-tert.butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol trimethylhexanediol, trimethylolethane, trimethylolpropane, tris-hydroxyethyl isocyanurate and 4-hydroxymethyl-1-phospha-2,6,7-trioxabicyclo[2,2,2]octane.

1.13. Acylaminophenols, such as, for example, N-(3,5-di-tert.butyl-4-hydroxyphenyl)-stearic acid amide, N,N'-di-(3,5di-tert.butyl-4-hydroxyphenyl)-thiobis-acetamide and thiophosphoric acid O,O-diethyl ester 3,5-di-tert.butyl-4-hydroxy anilide.

1.14. Benzylphosphonates, such as for example, 3,5-di-tert.butyl-4-hydroxybenzyl-phosphonic acid dimethyl ester, 3,5-di-tert.butyl-4-hydroxybenzyl-phosphonic acid diethyl ester, 3,5-di-tert.butyl-4-hydroxybenzyl-phosphonic acid dioctadecyl ester and 5-tert.butyl-4-hydroxy-3-methylbenzyl-phosphonic acid dioctadecyl ester.

1.15. Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-di-sec.buty-p-phenylenediamine, 6-ethoxy-2,2,4-trimethyl-1,2-dihydroquinoline, 6-dodecyl-2,2,4-trimethyl-1,2-dihydroquinoline, monooctyliminodibenzyl and dioctyliminodibenzyl and polymerised 2,2,4-trimethyl-1,2-dihydroquinoline. Octylated diphenylamine, nonylated diphenylamine, N-phenyl-N'-cyclohexyl-p-phenylenediamine, N-phenyl-N'-isopropyl-p-phenylenediamine, N,N'-di-sec.octyl-p-phenylenediamine, N-phenyl-N'-sec.octyl-p-phenylenediamine, N,N'-di-(1,4-dimethylpentyl)-p-phenylenediamine, N,N'-dimethyl-N,N'-di-(sec. octyl)-p-phenylenediamine, 2,6-dimethyl-4-methoxyaniline, 4-ethoxy-N-sec.butylaniline, the condensation product of diphenylamine and acetone, aldol-1-naphthylamine and phenothiazine.

2. UV absorbers and light stabilisers 2.1. 2-(2'-Hydroxyphenyl)-benztriazoles, such as, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 3'-α-methylbenzyl-5'-methyl-, 3'-α-methylbenzyl-5'-methyl-5-chloro-,4'-hydroxy-, 4'-methoxy-, 4'-octoxy-, 3,',5'-di-tert.amyl-, 3'-methyl-5'-carbomethoxyethyl- and 5-chloro-3',5'di-tert.-amyl-derivative.

2.2. 2,4-Bis-(2'-hydroxyphenyl)-6-alkyl-s-triazines, such as, for example, the 6-ethyl-, 6-heptadecyl or 6-undecyl-derivative.

2.3. 2-Hydroxy-benzophenones, such as, for example, the 4-hydroxy-, 4-methoxy, 4-octoxy, 4-decyloxy-, 4-dodecyloxy-, 4-benzyloxy, 4,2',4'-trihydroxy- and 2'-hydroxy-4,4'-dimethoxy-derivative.

2.4. 1,3-Bis-(2'-hydroxy-benzoyl)-benzenes, such as, for example, 1,3-bis-(2'-hydroxy-4'-hexyloxy-benzoyl)-benzene, 1,3-bis-(2'-hydroxy-4'-octyloxy-benzoyl)-benzene and 1,3-bis-(2'-hydroxy-4'-dodecyloxy-benzoyl)-benzene.

2.5. Esters of optionally substituted benzoic acids such as, for example, phenyl salicylate, octylphenyl salicylate, dibenzoylresorcinol, bis-(4-tert.-butylbenzoyl)-resorcinol, benzoylresorcinol and 3,5-di-tert.-butyl-4-hydroxybenzoic acid 2,4-di-tert.butyl-phenyl ester, octadecyl ester of 2-methyl-4,6-di-tert.butyl-phenyl ester.

2.6. Acrylates, such as, for example, α-cyano-β,β-diphenylacrylic acid ethyl ester or isooctyl ester, α-carbomethoxycinnamic acid methyl ester, α-cyano-β-methyl-β-methoxy-cinnamic acid methyl ester or butyl ester and N-(β-carbomethoxy-vinyl)-2-methyl-indoline.

2.7. Nickel compounds, such as, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel complexes of bis-[2-hydroxy-4-(1,1,3,3-tetramethylbutyl)-phenyl]-sulphone, such as 2:1 complex, optionally with additional ligands such as 2-ethyl-caproic acid, nickel dibutyldithiocarbamate, nickel salt of 4-hydroxy-3,5-di-tert.butylbenzyl-phosphonic acid monoalkyl esters, such as of the methyl, ethyl or butyl ester, nickel complexes of ketoxamines such as of 2-hydroxy-4-methyl-phenyl undecyl ketonoxime, nickel 3,5-di-tert.butyl-4-hydroxy-benzoate and nickel iospropylxanthate.

2.8. sterically hindered amines, such as, for example, 4-benzoyloxy-2,2,6,6-tetramethylpiperidine, 4-stearoyloxy-2,2,6,6-tetramethylpiperidine, bis-(2,2,6,6-tetramethylpiperidyl)-sebacate and 3-n-octyl-7,7,9,9-tetramethyl-1,3,8-triaza-spiro[4,5]decane-2,4-dione.

2.9. Oxalic acid diamides, such as, for example, 4,4'-di-octyloxy-oxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis-(3-dimethylaminopropyl)-oxalamide, 2-ethoxy-5-tert.butyl-2'-ethyl-oxanilide and its mixture with 2-ethoxy-2'-ethyl-5,4'-di-tert.butyl-oxanilide and mixtures of ortho- and para-methoxy- as well as of o- and p-ethoxydisubsituted oxanilides.

3. Metal deactivators, such as, for example, oxanilide, isophthalic acid dihydrazide, sebacic acid bis-phenylhydraxide, bis-benzylidene-oxalic acid dihydrazide, N,N'-diacetyl-adipic acid dihydrazide, N,N'-bis-salicyloyloxalic acid dihydrazide, N,N'-bis-salicyloylhydrazine, N,N'-bis-(3,5-di-tert.butyl-4-hydroxyphenyl-propionyl)-hydrazine, N-salicyloyl-N'-salicylalhydrazine, 3-salicyloylamino-1,2,4-triazole and N,N'-bis-salicyloyl-thiopropionic acid dihydrazide.

4. Phosphites, such as, for example, triphenyl phosphite, diphenylalkyl phosphites, phenyldialkyl phosphites, tri-(nonylphenyl) phosphite, trilauryl phosphite, trioctadecyl phosphite, 3,9-di-isocdecyloxy-2,4,8,10-tetraoxa-3,9-diphosphaspiro[5,5]-undecane and tri-(4-hydroxy-3,5-di-tert.butylphenyl) phosphite.

5. Compounds which destroy peroxide, such as, for example, esters of β-thiodipropionic acid, for example the lauryl, stearyl, myristyl or tridecyl esters, mercapto-benzimidazole or the zinc salt of 2-mercapto-benzimidazole.

6. Polyamide stabilisers, such as, for example, copper salts in combination with iodides and/or phosphorus compounds and salts of divalent manganese.

7. Basic co-stabilisers, such as, for example, melamine, benzoguanamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example Ca stearate, Zn stearate, Mg stearate, Na ricinoleate and K palmitate, antimony pyrocatecholate or zinc pyrocatecholate.

8. PVC stabilisers, such as, for example, organic tin compounds, organic lead compounds and barium-cadmium salt of fatty acids.

9. Nucleating agents, such as, for example, 4-tert.butyl-benzoic acid, adipic acid and diphenylacetic acid.

10. Urea derivatives, such as, for example, N-cyclohexyl-N'-1-naphthylurea, N-phenyl-N,N'-dicyclohexylurea, N-phenyl-N'-2-naphthylurea, N-phenylthiourea and N,N'-dibutylthiourea.

11. Other additives, such as, for example, plasticisers, lubricants, emulsifiers, fillers, carbon black, asbestos, kaoline, talc, glass fibres, pigments, optical brighteners, flameproofing agents and antistatic agents.

The invention is described in greater detail in the examples which follow. In these, percentage (%) denotes percentage by weight.

EXAMPLE 1

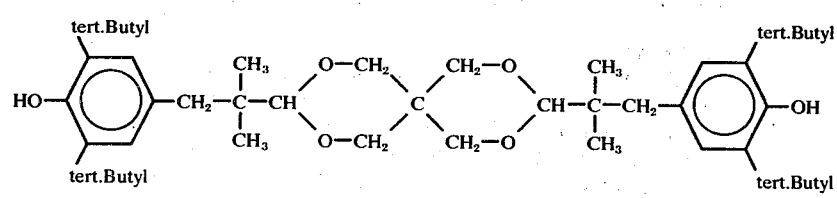

29.04 g (0.1 mol) of 3-(3,5-di-tert.butyl-4-hydroxyphenyl)-2,2-dimethyl-propionaldehyde, 6.8 g (0.05 mol) of pentaerythritol and 0.5 g of p-toluenesulphonic acid in 150 ml of toluene are heated under reflux for 2 hours under a water separator. During this time approx. 1.8 ml of water separate out. The mixture is then cooled and the toluene solution is washed with water and concentrated to dryness. The residual resin is recrystallised from hexane. This gives 3,9-bis[1,1-dimethyl-2-(3,5-di-tert.butyl-4-hydroxyphenyl)-ethyl]-2,4,8,10-tetra-oxaspiro[5,5]-undecane, of melting point: 194° C (stabiliser No. 1).

If, in this example, the pentaerythritol is replaced by an equimolecular amount of the polyols or polythiols of Table 1 below (first column), an otherwise identical procedure gives the acetals or thioacetals (second column) having the melting points indicated.

(0.05 mol) of pentaerythritol and 0.5 g of p-toluenesulphonic acid in 150 ml of toluene are heated under reflux for 2 hours under a water separator. Approx. 1.8 ml of water separate out during this time. After cooling, the toluene solution is washed with water and concentrated. The residue is recrystallised from hexane. This gives 3,9-bis[1,1-dimethyl-2-(3-tert.butyl-4-hydroxy-5-methylphenyl)ethyl]-2,4,8,10-tetraoxaspiro[5,5]-undecane, of melting point 146° C (stabiliser No. 7).

If, in this example, the pentaerythritol is replaced by an equimolecular amount of the polyols in Table 2 below (first column), an otherwise identical procedure gives the cyclic acetals (second column) having the melting points indicated.

Table 1

| Polyol | Product | Melting point | Stabiliser No. |
|---|---|---|---|
| HS—CH₂, CH₂—SH / C / HS—CH₂, CH₂—SH | R—CH(S—CH₂)₂C(CH₂—S)₂CH—R | 224° C | 2 |
| HO—CH₂, CH₂—OH / C / HO—CH₂, C₂H₅ | R—CH(O—CH₂)C(CH₂—OH)(O—CH₂)(C₂H₅) | 116° C | 3 |
| HO—CH₂, CH₂—OH / C / HO—CH₂, CH₃ | R—CH(O—CH₂)C(CH₂—OH)(O—CH₂)(CH₃) | 144° C | 4 |
| HO—CH₂, C₂H₅, C₂H₅, CH₂—OH / C—C / HO—CH₂, CH₂—O—CH₂, CH₂—OH | [R—CH(O—CH₂)C(C₂H₅)(O—CH₂)(CH₂—)]₂—O | 196° C | 5 |
| HO—CH₂, H, OH, CH₂—OH / C—C / HO—CH₂, CH₂, CH₂—OH / CH₂ / CH₂ | R—CH(O—CH₂)C(H)(OH)C(CH₂—O)(CH₂—O)CH—R / CH₂ / CH₂ | 220° C | 6 |

$$R = HO{-}\underset{\text{tert.Butyl}}{\overset{\text{tert.Butyl}}{\bigcirc}}{-}CH_2{-}\underset{CH_3}{\overset{CH_3}{C}}{-}$$

EXAMPLE 2

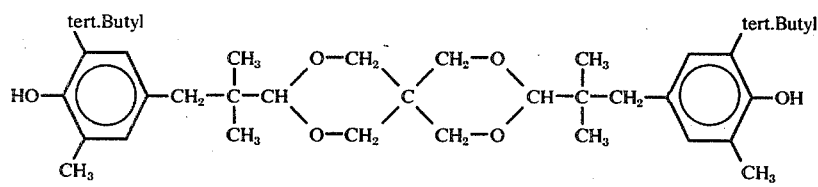

24.8 g (0.1 mol) of 3-(3-tert.butyl-4-hydroxy-5-methylphenyl)-2,2-dimethyl-propionaldehyde, 6.8 g Table 2

| Polyol | Product | Melting point | Stabiliser No. |
|---|---|---|---|
| HO—CH₂, CH₂—OH / C / HO—CH₂, C₂H₅ | R—CH(O—CH₂)C(CH₂—OH)(O—CH₂)(C₂H₅) | 105° C | 8 |

Table 2-continued

| Polyol | Product | Melting point | Stabiliser No. |
|---|---|---|---|
| 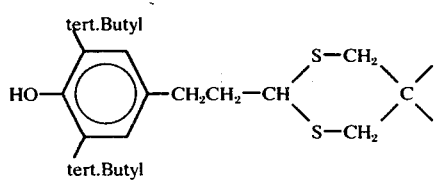 | (structure with R—CH, O—CH₂, C, CH₃, CH₂—OH, O—CH₂) | 92° C | 9 |

R= HO—[ring with tert.Butyl groups and CH₃]—CH₂—C(CH₃)₃

EXAMPLE 3

[Structure: HO—(tert.Butyl substituted phenyl)—CH₂CH₂—CH(S—CH₂)₂C(CH₂—S)₂CH—CH₂CH₂—(tert.Butyl substituted phenyl)—OH]

2 g (0.01 mol) of tetrathiopentaerythritol, 5.25 g (0.02 mol) of 3-(;b 3,5-di-tert.butyl-4-hydroxyphenyl)-propionaldehyde and 0.1 g of -toluenesulphonic acid are dissolved in 50 ml of benzene and are heated to reflux temperature for 30 minutes under a water separator. The mixture is then cooled and the benzene solution is washed with water and concentrated to dryness. The residue is dissolved in methanol by heating. On cooling, 3,9-bis-[2-(3,5-di-tert.butyl-4-hydroxyphenyl)ethyl]-2,4,8,10-tetra-thia-spiro[5,5]undecane, of melting point 154° C (stabiliser No. 10) crystallises out.

If, in this example, the tetra-thio-pentaerythritol is replaced by an equimolecular amount of pentaerythritol, an otherwise identical procedure gives 3,9-bis-[-(2-(3,5-di-tert.butyl-4-hydroxyphenyl)-ethyl]-2,4,8,10-tetra-oxa-spiro[5,5]undecane, of melting point 167° C (stabiliser No. 11).

EXAMPLE 4

100 parts of polypropylene (melt index 3.2 g/10 minutes, 230° C/2160 g) are intensively mixed for 10 minutes, in a shaking apparatus, with 0.2 part of an additive listed in Table 3 which follows. The resulting mixture is kneaded in a Brabender plastograph for 10 minutes at 200° C and the composition obtained in this way is then pressed in a platen press at a platen temperature of 260° C to give sheets 1 mm thick, from which strips 1 cm wide and 17 cm long are punched.

The effectiveness of the additives added to the test strips is tested by heat ageing in a circulating air oven at 135° and 149° C, an additive-free test strip being used as a comparison. 3 test strips of each formulation are employed for this purpose. The end point is defined as the incipient, easily visible, crumbling of the test strip.

Table 3

| Stabiliser No. | Days before decomposition begins | |
|---|---|---|
| | 149° C | 135° C |
| None | <1 | ~3 |
| 1 | 6 | 50 |
| 2 | 16 | 69 |
| 5 | 3 | 44 |
| 6 | 3 | 40 |
| 7 | 7 | 82 |
| 10 | 30 | 97 |
| 11 | 24 | 105 |

EXAMPLE 5

100 parts of polypropylene (melt index 3.2 g/10 minutes, 230° C/2160 g) are intensively mixed for 10 minutes, in a shaking apparatus, with 0.1 part of an additive listed in Table 4 which follows and 0.3 part of dilauryl thiodipropionate.

The resulting mixture is kneaded for 10 minutes in a Brabender plastograph at 200° C and the composition obtained in this way is then pressed in a platen press at a platen temperature of 260° C to give sheets 1 mm thick, from which strips 1 cm wide and 17 cm long are punched.

The effectiveness of the additives added to the test strips is tested by heat ageing in a circulating air oven at 135° C and 149° C, a test strip which contains only 0.3 part of dilauryl thiodipropionate being used as a comparison. Three test strips of each formulation are employed for this purpose. The end point is defined as the incipient, easily visible, crumbling of the test strip.

Table 4

| Stabiliser | Days before decomposition begins | |
|---|---|---|
| | 149° C | 135° C |
| None | 5 | 11 |
| 1 | 33 | 171 |
| 2 | 42 | 117 |
| 5 | 25 | 96 |
| 6 | 34 | 117 |
| 7 | 46 | 124 |
| 10 | 35 | 112 |
| 11 | 27 | 159 |

EXAMPLE 6

The test pieces described in Example 4 were tested for colour stability, in particular:
a. After incorporation (Table 5, column 2)
b. After 500 hours' exposure in a Xenotest apparatus of Messrs. Hanau (Table 5, column 3)
c. After treatment with boiling water for 1 week (Table 5, column 4).

An empirical colour scale in which 5 denotes absence of colour, 4 denotes a slight discolouration which is just noticeable, and 3, 2, 1 and <1 denote a successively greater discolouration, was used for Table 5.

Table 5

| Stabiliser No. | Colour assessment according to scale 1–5 | | |
|---|---|---|---|
| | After incorporation | After exposure | Boiling water for 1 week |
| None | 5 | 5 | 5 |
| 1 | 4–5 | 5 | 4–5 |
| 2 | 4–5 | 4–5 | 4–5 |
| 5 | 4–5 | 5 | 5 |
| 6 | 4–5 | 5 | 4–5 |
| 7 | 5 | 5 | 5 |
| 10 | 4 | 4–5 | 4 |
| 11 | 4–5 | 5 | 5 |

EXAMPLE 7

The test pieces described in Example 5 were tested for colour stability, in particular:
a. After incorporation (Table 6, column 2)
b. After 500 hours' exposure in a Xenotest apparatus of Messrs. Hanau (Table 6, column 3)
c. After treatment with boiling water for 1 week (Table 6, column 4)

An empirical colour scale in which 5 denotes absence of colour, 4 denotes a slight discolouration which is just noticeable, and 3, 2, 1 and <1 denote a successively greater discolouration, was used for Table 6.

Table 6

| Stabiliser No. | Colour assessment according to scale 1–5 | | |
|---|---|---|---|
| | After incorporation | After exposure | Boiling water for 1 week |
| None | 5 | 5 | 5 |
| 1 | 5 | 5 | 5 |
| 2 | 5 | 5 | 5 |
| 5 | 5 | 5 | 4–5 |
| 6 | 5 | 5 | 5 |
| 7 | 5 | 5 | 5 |
| 10 | 4–5 | 4–5 | 4 |
| 11 | 5 | 5 | 4–5 |

EXAMPLE 8

Shavings (chips) 25 $\mu$ thick are cut from the 1 mm thick test sheets described in Example 4 with the aid of a microtome. These chips are clamped between stainless steel grids and the sample carriers thus obtained are hung in a circulating air oven and are aged at 135° C or at 147° C. The end point is defined as the time after which degraded polypropylene falls out in a pulverised form if the grids are tapped gently (checked 1 – 2 times daily). The results are quoted in hours (Table 7).

Table 7

| Stabiliser No. | Hours before decomposition begins | |
|---|---|---|
| | at 147° C | at 135° C |
| without additive | 2 | 10 |

Table 7-continued

| Stabiliser No. | Hours before decomposition begins | |
|---|---|---|
| | at 147° C | at 135° C |
| 2 | 65 | 240 |
| 10 | 140 | 440 |
| 11 | 70 | 210 |

EXAMPLE 9

Shavings (chips) 25 $\mu$ thick are cut from the 1 mm thick test sheets described in Example 5 with the aid of a microtome. These chips are clamped between stainless steel grids and the sample carriers thus obtained are hung in a circulating air oven and are aged at 135° C or at 147° C. The end point is defined as the time after which degraded polypropylene falls out in a pulverised form if the grids are tapped gently (checked 1 – 2 times daily). The results are quoted in hours (Table 8).

Table 8

| Stabiliser No. | Hours before decomposition begins | |
|---|---|---|
| | at 147° C | at 135° C |
| comparison | 10 | 20 |
| 2 | 42 | 117 |
| 10 | 165 | 500 |
| 11 | 100 | 240 |

EXAMPLE 10

Stabilisation of polyamide 6

100 parts of polyamide 6 granules (Perlon, unbleached, containing 1% of $TiO_2$, ex Glanzstoff, AG, relative viscosity of a 1% strength solution in concentrated sulphuric acid = 2.9) are mixed dry with 0.5 part of an additive listed in Table 9 which follows, and are melted under nitrogen for 30 minutes at 270° C in a glass tube. Samples are taken from the melt reguli and are pressed at 260° C to give test films 0.3 mm thick. The films are subjected to an accelerated ageing in a circulating air oven at 165° C. The degradation of the material is followed by periodically measuring the relative viscosity of a 1% strength solution in concentrated sulphuric acid. The time during which the relative viscosity falls to 1.7 from the initial value of 2.9 is determined as the end point (Table 9).

Table 9

| Stabiliser No. | Ageing time. Decrease in relative viscosity from 2.9 to 1.7 |
|---|---|
| without stabiliser | 14 hours |
| 1 | 31 hours |
| 11 | 43 hours |

EXAMPLE 11

Protection of polyacrylonitrile (PAN) from yellowing 0.5 part of stabiliser 1, together with 25 parts of PAN, are dissolved in 75 parts of dimethylformamide (DMF) at 70° C for 4 hours. The stabilised solution exhibits, even on visual comparison, a distinctly lighter colour than the additive-free solution. Films approx. 500 $\mu$ thick are drawn from these solutions on a glass plate and the films are dried at 125° C for 10 minutes.

The degree of yellowing of the dried films is assessed visually on a white background as follows:

Table 10

| | Discolouration |
|---|---|
| Comparison colour without additive | yellow |
| 0.5% of stabiliser 1 | white with a very faint yellowish tinge |

The same results are obtained if, instead of dimethylformamide, other solvents, such as, for example, an ethylene carbonate-water mixture (80:20) are used.

EXAMPLE 12

Stabilisation of ABS 0.3% of stabiliser 1 are sprinkled onto unstabilised ABS resin and the sprinkled mixture is re-granulated at 240° C on a single-screw extruder. Granules are prepared in the same way with no addition of stabiliser 1, for comparison. The granules are injection-moulded into small sheets in the customary manner on an injection moulding machine at 250° C. The sheets are aged for 10 days in a circulating air oven at 80° C and the colour behaviour is assessed.

Table 11

| | Colour of the sheets | |
|---|---|---|
| | Initial condition | After 10 days at 80° C |
| without stabiliser | yellow-beige | yellow-brownish light beige |
| 0.3% of stabiliser 1 | light beige | light beige |

The addition of 0.3% of stabiliser 1 improves the colour of ABS in its initial condition and prevents discolouration during the oven ageing process.

EXAMPLE 13

1,000 parts of polypropylene powder [melt index 20 (230° C, 2,160 g)] are mixed with 2 parts of stabiliser No. 1 at 200° C in a Brabender kneader.

The mixture homogenised in this way is taken out of the kneader and is pre-pressed by means of a toggle press into sheets 2-3 mm thick, which are then converted at 260° C, in a heated platen press, using suitable matrices, first into films 0.3 mm thick and, in a further operation, into films 0.1 mm thick.

The films produced in this way are heat-treated for 1 hour at 150° C, avoiding cooling below 150° C, and directly afterwards are chilled in water at 15° C. The films produced in this way have a homogeneous structure with fine spherulites. Test pieces punched from them have an elongation of approx. 800%.

The film used as a comparison is produced in the same manner using 2 parts of 1,3,5-tris(3,5-di-tert.-butyl-4-hydroxybenzyl)-isocyanurate.

Table 12

| Stabiliser No. | Hours of exposure in Xenotest for the elongation at break to decline to 50% of its initial value |
|---|---|
| 1 | 1680 |
| 1,3,5-tris-(3,5-di-tert.-butyl-4-hydroxy-benzyl)-isocyanurate | 1120 |

What we claim is:

1. A compound of the formula

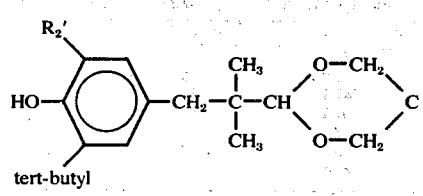

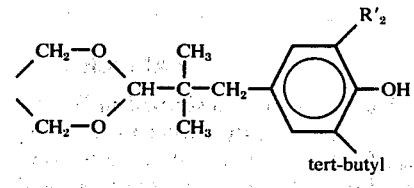

in which $R_2'$ denotes methyl, isopropyl or tert-butyl.

2. Compound according to claim 1 of the formula,

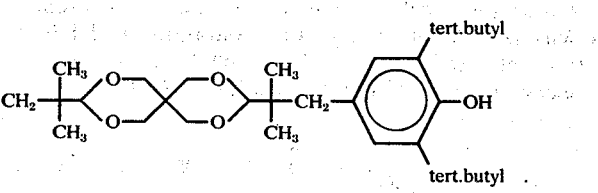

3. Compound according to claim 1 of the formula,

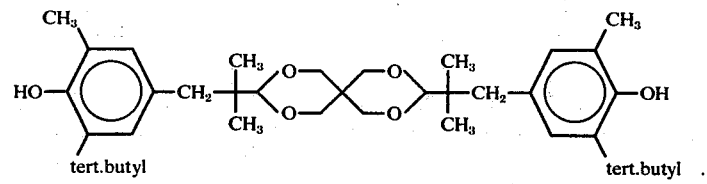

4. A composition of matter comprising an organic polymer subject to oxidative degradation containing 0.005 to 5% by weight of a stabilizer compound of the formula

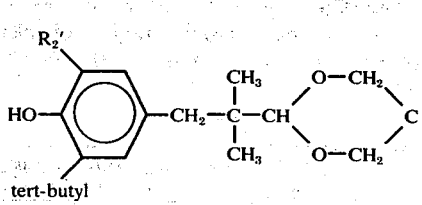

-continued
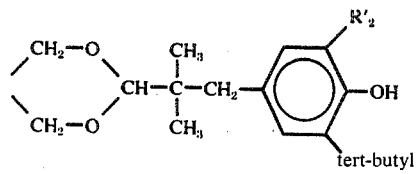
which R'₂ denotes methyl, isopropyl or tert-butyl.
5. A composition according to claim 4, containing a compound of the formula,
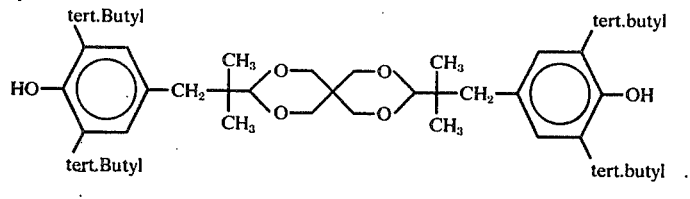
6. A composition according to claim 4, containing a compound of the formula,
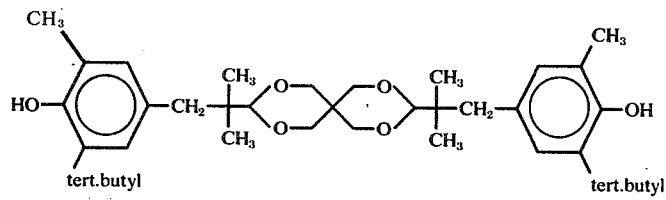
* * * * *